United States Patent [19]

Hagmann

[11] Patent Number: 4,622,407

[45] Date of Patent: Nov. 11, 1986

[54] RESOLUTION OF RACEMIC DERIVATIVES OF 5-(1-METHYL-5-METHYLTHIOPYRROL-2-OYL)-1,2-DIHYDRO-3H-PYRROLO[1,2-A]PYRROLE-2-CARBOXYLIC ACID AND ANALOGS

[75] Inventor: William K. Hagmann, Westfield, N.J.

[73] Assignee: Merck & Co., Inc., Rahway, N.J.

[21] Appl. No.: 604,277

[22] Filed: Apr. 26, 1984

[51] Int. Cl.$^4$ .......................................... C07D 487/06
[52] U.S. Cl. .................................... 548/453
[58] Field of Search ........................................ 548/453

[56] References Cited

U.S. PATENT DOCUMENTS 4,089,969  5/1978  Muchowski et al. ............... 548/453

OTHER PUBLICATIONS

Gilman, vol. 1, Org. Chem., pp. 194–195 (1938).
B. Neises et al., Agnew. Chem. Int. Ed. Engl., 17, 522 (1978).

*Primary Examiner*—Glennon H. Hollrah
*Assistant Examiner*—D. B. Springer
*Attorney, Agent, or Firm*—Theresa Y. Cheng; Michael C. Sudol

[57] ABSTRACT

Racemic mixture of derivatives of 5-(1-methyl-5-methylthiopyrrol-2-oyl)-1,2-dihydro-3H-pyrrolo[1,2-a]pyrrole-2-carboxylic acid and analogs were resolved into pure l- or d-isomers via concomitant isomerization and functional crystallization.

5 Claims, No Drawings

RESOLUTION OF RACEMIC DERIVATIVES OF 5-(1-METHYL-5-METHYLTHIOPYRROL-2-OYL)-1,2-DIHYDRO-3H-PYRROLO[1,2-a]PYRROLE-2-CARBOXYLIC ACID AND ANALOGS

BACKGROUND OF THE INVENTION

The present invention relates to a novel process whereby the racemic derivatives of a substituted 5-(pyrrol-2-oyl)-1,2-dihydro-3H-pyrrolo[1,2-a]pyrrole-1-carboxylic acid are separated via a unique resolution method into pure l- and d-isomers. Derivatives of substituted 5-(pyrrol-2-oyl)-1,2-dihydro-3H-pyrrolo[1,2-a]pyrrole-1-carboxylic acid are disclosed in U.S. Pat. No. 4,511,724 issued to Michael N. Chang and Tesfaye Biftu. These compounds are useful as anti-inflammatory and analgesic agents.

Previously, the separation of a racemic mixture of diastereomers could be accomplished by high pressure liquid chromatography (HPLC) and fractional crystallization. However, the overall yield of these well-established methods, as applied to compounds referred to in the present invention, are very poor. In particular, the HPLC method is impractical when large quantities of a pure diastereomer are required.

It has been known that by relying on the difference in solubilities of two diastereomers in a chosen solvent system, efficient separation can be achieved. Applying this principle to the compounds referred to in the present invention, for example, ethyl 5-(1-methyl-5-methylthiopyrrol-2-oyl)-1,2-dihydro-6-methyl-3H-pyrrolo[1,2-a]pyrrole-1-carboxylate, a 83% improvement of yield over the conventional methods was observed.

DETAILED DESCRIPTION OF THE INVENTION

The compounds to be resolved by the novel process of the present invention are of the formula (I):

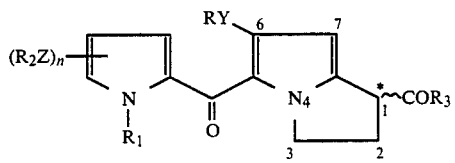

*asymmetric center

R is
- (a) hydrogen;
- (b) loweralkyl especially $C_{1-6}$ linear or branched alkyl such as methyl, ethyl, propyl, isopropyl, t-butyl, pentyl, and hexyl;
- (c) lowercycloalkyl especially $C_{3-6}$ cycloalkyl such as cyclopropyl, cyclobutyl, cyclopentyl and cyclohexyl;
- (d) lower(cycloalkyl-alkyl) especially $C_{4-8}$ (cycloalkyl-alkyl) such as cyclopropylmethyl, cyclopentylmethyl, cyclohexylmethyl and cyclohexylethyl;
- (e) loweralkenyl especially $C_{2-8}$ alkenyl such as 2-propenyl, 2-methyl-2-butenyl and 3-ethyl-2-pentenyl;
- (f) halo-loweralkyl especially halo $C_{1-6}$ alkyl such as chloromethyl, trifluoromethyl, 1-chloroethyl and 2,2-difluorobutyl; or
- (g) phenyl- or substituted phenyl-loweralkyl especially phenyl-$C_{1-3}$ alkyl such as benzyl, 4-chlorobenzyl, 2-fluorobenzyl, and phenylpropyl.

groups (a)–(g) above being unsubstituted or substituted by loweralkyl, loweralkoxy, halo, cyano, carboxy, sulfonamino, carbamoyl, loweralkyl or amino sulfonyl, loweralkyl or aminosulfinyl, azido, amino, substituted amino such as loweralkylamino or diloweralkylamino, haloalkyl, carboxyalkyl, carbamoylalkyl, N-substituted carbamoylalkyl or a combination thereof;

$R^1$ is hydrogen, haloloweralkyl or loweralkyl especially $C_{1-6}$ alkyl as previously defined;

$R^2Z$ can be at any available ring positions and $R^2$ is R as previously defined;

n is 1 to 3;

$R^3$ is
- (a) hydroxy;
- (b) loweralkoxy especially $C_{1-6}$ alkoxy as defined previously;
- (c) amino;
- (d) loweralkylamino especially $C_{1-6}$ alkylamino such as cyclohexylamino, methylamino, isopropyl amino, n-butylamino or t-butylamino;
- (e) diloweralkylamino especially di($C_{1-6}$ alkyl)amino such as diethylamino, or dimethylamino;
- (f) morpholinyl;
- (g) bis(hydroxyloweralkyl)amino especially bis(hydroxy $C_{1-6}$ alkyl)amino such as bis(hydroxyethyl)amino;
- (h) loweralkylcyclohexylamino especially $C_{1-6}$ alkylcyclohexylamino such as methylcyclohexylamino; or
- (i) glucosamino;
- (j) lower(alkanoyloxyalkoxy), especially $C_{1-6}$ (alkanoyloxyalkoxy) such as 1-(pivaloyloxy)ethoxy or 1-(acetoxy)ethoxy;
- (k) aroyloxyloweralkoxy especially 1-(benzoxy)ethoxy;
- (l) lower(alkoxycarbonyloxyalkoxy) especially $C_{1-6}$ (alkoxycarbonyloxyalkoxy) such as 1-(ethoxycarbonyloxy)ethoxy;
- (m) aryloxycarbonyloxyloweralkoxy especially aryloxycarbonyloxy $C_{1-6}$ alkoxy such as 1-(benzyloxycarbonyloxy)ethoxy;
- (n) tri(loweralkylamino)loweralkoxy especially tri ($C_{1-6}$ alkylamino) $C_{1-6}$ alkoxy such as cholineoxy;
- (o) lower(alkanoylaminoalkoxy), especially $C_{1-6}$ (alkanoylaminoalkoxy) such as acetamidoethoxy;
- (p) imidoloweralkoxy especially imido $C_{1-6}$ alkoxy such as 1-(succinimido)ethoxy;
- (q) heterocyclyloxy, for example, phthalidyloxy, or 2-pyridyloxy;
- (r) hydroxyloweralkoxy especially hydroxy $C_{1-6}$ alkoxy such as hydroxypropoxy;
- (s) loweralkoxyalkoxy especially $C_{1-6}$ (alkoxyalkoxy) such as methoxyethoxy, ethoxyethoxy or methoxymethoxy;
- (t) di(loweralkylamino)loweralkoxy especially di($C_{1-6}$alkylamino) $C_{1-6}$ alkoxy such as dimethylamino ethoxy, dimethylamino-propoxy, or diethylamino propoxy;
- (u) N-pyrrolidinylloweralkoxy especially N-pyrrolidinyl $C_{1-6}$ alkoxy such as N-pyrrolidinylethoxy or N-pyrrolidinyl methoxy and N-methyl-2-pyrrolidinylmethoxy;

(v) N-piperidinylloweralkoxy especially N-piperidinyl $C_{1-6}$ alkoxy such as N-piperidinylethoxy;

(w) N-morpholinylloweralkoxy especially N-morpholinyl $C_{1-6}$alkoxy such as N-morpholinylethoxy; or (x) 4-methyl-1-piperazinylloweralkoxy especially 4-methyl-1-piperazinyl $C_{1-6}$ alkoxy such as 4-methyl-1-piperazinylethoxy;

Y is oxygen, sulfur, sulfinyl, sulfonyl, $CH_2$— or hydrogen providing that when Y is hydrogen, R does not exist; and Z is —O—, —S—, —SO—, —SO$_2$—, —NH—, —CH$_2$ or halo especially fluoro, chloro or bromo providing that when Z is halo, $R^2$ does not exist.

The preferred embodiment of this invention comprises the process for resolving compounds of formula (I) wherein R is
(a) hydrogen or $C_{1-6}$ alkyl as previously defined;
(b) $C_{2-4}$ alkenyl such as 2-propenyl or propenylmethyl;
(c) halo-$C_{1-6}$ alkyl as previously defined; or
(d) phenyl-$C_{1-3}$ alkyl such as benzyl;

$R^1$ is hydrogen or $C_{1-6}$ alkyl;

$R^2Z$ is at position 5, i.e. adjacent to N and is R as defined above;

n is 1;

$R^3$ is hydroxy, $C_{1-6}$ alkoxy, or lower(alkanoylaminoalkoxy), especially $C_{1-6}$ alkanoylaminoalkoxy such as acetamidoethoxy;

Y is oxygen, sulfur, $CH_2$—, or H when R is absent; and

Z is —S—, —CH$_2$—, or halo when $R^2$ is absent.

The most preferred embodiment of this invention comprises the process for the resolving compounds of structural formula (I) wherein R is $C_{1-3}$ alkyl especially methyl or absent;

$R^1$ is hydrogen or methyl;

$R^2Z$ is at position 5 and $R^2$ is hydrogen, methyl, or absent;

n is 1;

$R^3$ is hydroxy, $C_{1-6}$ alkoxy or acetamidoethoxy;

Y is oxygen, $CH_2$—, or H with the proviso that when Y is H, R is absent; and

Z is —S—, —CH$_2$—, or halo with the proviso that when Z is halo, $R^2$ is absent.

The representative compounds which can be resolved to pure d- or l-isomer by the process of the present invention comprise:

(1) 5-(5-methylthio-2-pyrroyl)-1,2-dihydro-6-methyl-3H-pyrrolo[1,2-a]pyrrole-1-carboxylic acid;
(2) ethyl 5-(5-methylthio-2-pyrroyl)-1,2-dihydro-6-methyl-3H-pyrrolo[1,2-a]pyrrole-1-carboxylate;
(3) 5-(5-chloro-2-pyrroyl)-1,2-dihydro-6-methyl-3H-pyrrolo[1,2-a]pyrrole-1-carboxylic acid; or
(4) ethyl 5-(5-chloro-2-pyrroyl)-1,2-dihydro-6-methyl-3H-pyrrolo[1,2-a]pyrrole-1-carboxylate;
(5) 5-(5-isopropyl-2-pyrroyl)-1,2-dihydro-6-methyl-3H-pyrrolo[1,2-a]pyrrole-1-carboxylic acid;
(6) ethyl 5-(5-isopropyl-2-pyrroyl)-1,2-dihydro-6-methyl-3H-pyrrolo[1,2-a]pyrrole-1-carboxylate; or
(7) 5-(1-methyl-5-methylthio-2-pyrroyl)-1,2-dihydro-6-methyl-3H-pyrrolo[1,2-a]pyrrole-1-carboxylic acid;
(8) ethyl 5-(1-methyl-5-methylthio-2-pyrroyl-1,2-dihydro-6-methyl-3H-pyrrolo[1,2-a]pyrrole-1-carboxylate;
(9) 5-(1-methyl-5-chloro-2-pyrroyl)-1,2-dihydro-6-methyl-3H-pyrrolo[1,2-a]pyrrole-1-carboxylic acid;
(10) ethyl 5-(1-methyl-5-chloro-2-pyrroyl)-1,2-dihydro-6-methyl-3H-pyrrolo[1,2-a]pyrrole-1-carboxylate;
(11) 5-(1-methyl-5-isopropyl-2-pyrroyl)-1,2-dihydro-6-methyl-3H-pyrrolo[1,2-a]pyrrole-1-carboxylic acid;
(12) ethyl 5-(1-methyl-5-isopropyl-2-pyrroyl)-1,2-dihydro-6-methyl-3H-pyrrolo[1,2-a]pyrrole-1-carboxylate;
(13) 5-(1-methyl-5-ethylthio-2-pyrroyl)-1,2-dihydro-6-methyl-3H-pyrrolo[1,2-a]pyrrole-1-carboxylic acid;
(14) 5-(1-methyl-5-n-propylthio-2-pyrroyl)-1,2-dihydro-6-methyl-3H-pyrrolo[1,2-a]pyrrole-1-carboxylic acid;
(15) 5-(1-methyl-5-methoxy-2-pyrroyl)-1,2-dihydro-6-methyl-3H-pyrrolo[1,2-a]pyrrole-1-carboxylic acid;
(16) 5-(1-methyl-5-ethoxy-2-pyrroyl)-1,2-dihydro-6-methyl-3H-pyrrolo[1,2-a]pyrrole-1-carboxylic acid;
(17) 5-(1-methyl-5-n-propyloxy-2-pyrroyl)-1,2-dihydro-6-methyl-3H-pyrrolo[1,2-a]pyrrole-1-carboxylic acid;
(18) 5-(1-trifluoromethyl-5-methylthio-2-pyrroyl)-1,2-dihydro-6-methyl-3H-pyrrolo[1,2-a]pyrrole-1-carboxylic acid;
(19) ethyl-5-(1-methyl-5-ethylthio-2-pyrroyl)-1,2-dihydro-6-methyl-3H-pyrrolo[1,2-a]pyrrole-1-carboxylate;
(20) ethyl 5-(1-methyl-5-n-propylthio-2-pyrroyl)-1,2-dihydro-6-methyl-3H-pyrrolo[1,2-a]pyrrole-1-carboxylate;
(21) ethyl 5-(1-methyl-5-methoxy-2-pyrroyl)-1,2-dihydro-6-methyl-3H-pyrrolo[1,2-a]pyrrole-1-carboxylate;
(22) ethyl 5-(1-methyl-5-ethoxy-2-pyrroyl)-1,2-dihydro-6-methyl-3H-pyrrolo[1,2-a]pyrrole-1-carboxylate;
(23) ethyl 5-(1-methyl-5-n-propyloxy-2-pyrroyl)-1,2-dihydro-6-methyl-3H-pyrrolo[1,2-a]pyrrole-1carboxylate; or
(24) ethyl 5-(1-trifluoromethyl-5-methylthio-2-pyrroyl)-1,2- dihydro-6-methyl-3H-pyrrolo[1,2-a] pyrrole-1-carboxylate.

The following scheme illustrates the novel resolution process of the present invention:

Step (a)

(R)(+)-R°OH e.g., (I) $\xrightarrow{\text{(R)-(+)-}\alpha\text{-phenethyl alcohol}}{\text{DCC/DMAP}}$

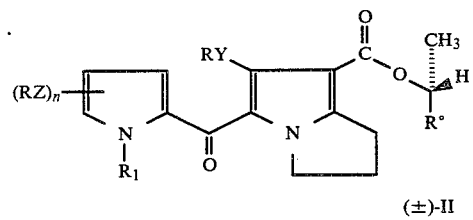

(±)-II wherein R° is α-phenethyl, asymmetric lower alkyl or the like;
DCC is dicyclohexylcarbodiimide; and DMAP is 4-dimethylaminopyridine.

Step (b)

(±)-II $\xrightarrow{\text{DBN}}$ (−)-II wherein DBN is 1,5-diazabicyclo[4.3.0]non-5-ene Step (c)

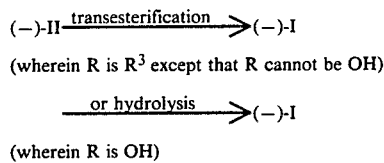

(wherein R is R³ except that R cannot be OH)

$\xrightarrow{\text{or hydrolysis}}$ (−)-I (wherein R is OH)

In step (a), formation of diastereomers can be accomplished by esterification with an optically pure asymmetric alcohol, for example, (R)-(+)-α-phenethyl alcohol. The esterification of carboxylic acids in the presence of carbodiimide and aminopyridine catalyst has been described in B. Neises and W. Steglich, *Angew. Chem. Int. Ed. Engl.*, 17, 522 (1978); A. Hassner and V. Alexanian, *Tet. Lett.*, 1978, 4475. Other methods employing isoureas for the formation of diastereomers may also be employed. For example, those methods described in L. J. Mathias, *Syn.*, 1979, 561. In addition, any other methods such as those describing the reaction of a carboxylic acid with an alcohol to form an ester may be used in the preparation of diastereomeric esters. See for example, I. T. Harrison, S. Harrison, "Compendium of Organic Synthetic Methods", Vols. 1 and 2, Wiley, New York, 1971 and 1974; L. S. Hegedus and L. Wade, ibid, Vol. 3, 1977; L. Wade, ibid, Vol. 4, 1980.

In step (b), the concomitant isomerization and fractional crystallization resulting in the resolution of (±)-II to the pure (−)-II isomer was effected by 1,5-diazabicyclo[4.3.0]non-5-ene (DBN) in host 25% ethyl acetate-hexane. Alternatively any strong, non-nucleophilic base may be substituted for DBN. The base must rapidly isomerize the diastereomers of II to a racemic mixture. This is, treatment of the 2:1 mixture of (±)-II with said base that results in a 1:1 mixture of (±)-II would be satisfactory for this reaction. The base must not effect hydrolysis of the ester. Examples of such bases would be lower trialkyl amines, for example, triethylamine and tri(n-butyl)amine, pyridine and substituted pyridines such as 2,4-dimethylpyridine, and imidoamines such as DBN and 1,8-diazabicyclo[5.4.0]undec-7-ene (DBU).

The choice of solvent is limited to that solvent or mixture of solvents in which the desired isomer is sparingly soluble. It is preferable that the desired isomer be soluble in the solvent when it is hot and insoluble when cool.

In step (c), an optically pure (−)-II ester is converted to a desired compound. Methods for the transesterification or hydrolysis of (−)-II were carefully chosen so as to avoid racemization of the very labile diastereomer. Therefore, methods employing basic conditions were avoided in favor of those using acid cleavage and low temperatures. It is reported that cleavage of a related system with trifluoroacetic acid (TFA) in benzene will give the optically pure carboxylic acid. J. M. Maclowski and A. F. Kluge, U.S. Pat. No. 4,089,969.

Strong Lewis acids, such as boron tribromide, boron trichloride, boron trifluoride etherate, aluminum chloride, aluminum bromide, tin (IV) chloride, and titanium (IV) chloride, in compatible solvents such as methylene chloride, chloroform, hexane, benzene, and toluene, at room temperature or lower were useful for effecting ester cleavage. Subsequent addition of an alcohol (R³OH) or water resulted in the formation of the ester (−)-II (R=R³) or acid (R=OH).

EXAMPLE 1

Isolation of Pure (−)-5-(1-Methyl-5-methylthiopyrrol-2-oyl)-1,2-dihydro-6-methyl-3H-pyrrolo[1,2-a]pyrrole-1-carboxylic acid

Step (a): Hydrolysis

A solution of (±)-ethyl 5-(1-methyl-5-methylthiopyrrol-2-oyl)-1,2-dihydro-6-methyl-3H-pyrrolo[1,2-a]pyrrole-2-carboxylate (0.50 g) in methanol (10 ml) and 10% sodium hydroxide (10 ml) were stirred at room temperature for 2 hours. A saturated sodium chloride solution was added to the solution and the methanol removed under reduced pressure. The aqueous solution was acidified with 3N hydrochloric acid with stirring and cooling and the resulting precipitate collected by filtration. The solids were washed with water, air dried, and recrystallized from ethyl acetate-hexane to give (±)-5-(1-methyl-5-methylthiopyrrol-2-oyl)-1,2-dihydro-6-methyl-3H-pyrrolo[1,2-a]pyrrole-1-carboxylic acid (0.45 g, 98% yield) m.p. 182°–184° C.

Step (b): Formation of Diastereomers

To a stirred suspension of (±)-5-(1-methyl-5-methylthiopyrrol-2-oyl)-1,2-dihydro-6-methyl-3H-pyrrolo[1,2-a]pyrrole-1-carboxylic acid (12.0 g, 37.7 mmol) in THF (70 ml) at 0° C. was added a solution of dicyclohexyl carbodiimide (8.56 g, 42.6 mmol) in $CH_2Cl_2$ (70 ml) and stirred 5 minutes at 0°. 4-Dimethylaminopyridine (0.52 g, 4.26 mmol) was added and then R-(+)-α-phenethyl alcohol (5.20 g, 42.6 mmol). The tan suspension was stirred at room temperature for 2.2 hours, and the washed filter cake was filtered with fresh $CH_2Cl_2$ (2×20 ml). Combined filtrates were washed successively with 1N HCl (3×20 ml), $H_2O$ (3×20 ml) and brine (1×), dried over $MgSO_4$, filtered and rotovapped to a brown residue, then chromatographed on a flash silica gel column (10×15 cm) eluted with 50% $Et_2O$/hexane to obtain the product as a yellow semisolid; a 1:2 mixture of 14.63 g of (±)-α-methylbenzyl 5-(1-methyl-5-methyl-thiopyrrol-2-oyl)-1,2-dihydro-6-methyl-3H-pyrrolo-[1,2-a]pyrrole-2-carboxylate (92%).

Step (c): Resolution

The mixture of (±)-α-methylbenzyl 5-(1-methyl-5-methylthiopyrrol-2-oyl)-1,2-dihydro-6-methyl-3H-pyrrolo[1,2-a]pyrrole-1-carboxylate (14.63 g, 34.6 mmol) was dissolved in hot 25% EtOAc/hexane (50 ml). 1,5-Diazabicyclo[4.3.0]non-5-ene (DBN) (5 drops) was added and the solution cooled slowly to room temperature. The solution was let stand at room temperature for 2 hours, filtered, and washed the precipitated with 15% EtOAc/hexane (3×20 ml). The solid was suspended in 25% EtOAc/hexane (70 ml) and heated to reflux, cooled in ice and filtered. The solid was washed again with 15% EtOAc/hexane to afford 12.88 g (88%) of (−)-α-methylbenzyl 5-(1-methyl-5-methylthiopyrrol-2-oyl)--1,2-dihydro-6-methyl-3H-pyrrolo[1,2-a]pyrrole-1-carboxylate. $[\alpha]_D^{25} = -111.3°$ ($CHCl_3$, C=1.21); m.p. 122°–123° C.

Step (d): Conversion to the Desired Compound

To a solution of (−)-α-methylbenzyl 5-(1-methyl-5-methylthiopyrrol-2-oyl)-1,2-dihydro-6-methyl-3H-pyrrolo[1,2-a]pyrrole-1-carboxylate (3.0 g, 7.1 mmol) in $CH_2Cl_2$ (80 ml) at −78° C. under $N_2$ atmosphere was slowly added a 1.0M solution of boron tribromide in $CH_2Cl_2$ (15.6 ml, 15.6 mmol). The solution was stirred at $-78°$ C. for 5 minutes and absolute ethanol (30 ml) was added slowly and warmed to room temperature then stirred at room temperature for 2 hours. The solution was washed with water ($3\times25$ ml.) and brine ($1\times25$ ml.), dried over anhydrous sodium sulfate, filtered and rotovapped at 20° C. to an orange solid and chromatographed on a flash silica gel column ($5\times15$ cm) eluted with 50% ether/hexane. The resulting crude product was crystallized from hot EtOH to afford 2.12 g (86% yield) of (−)-ethyl 5-(1-methyl- 5-methylthiopyrrol-2-oyl)-1,2-dihydro-6-methyl-3H-pyrrolo[1,2-a]pyrrole-1-carboxylate. $[\alpha]_D^{25} = -127.4$ ($CHCl_3$, C=1.06); m.p. 113°–115° C.

What is claimed is:

1. A process for resolving the racemic mixture of a compound of the structural formula:

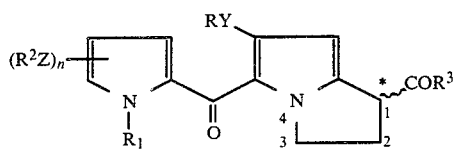

*asymmetric center wherein
R is
(a) H or $C_{1-6}$alkyl;
(b) $C_{2-4}$alkenyl;
(c) halo-$C_{1-6}$alkyl; or
(d) phenyl-$C_{1-3}$alkyl;
$R^1$ is hydrogen or $C_{1-6}$alkyl;
$R^2Z$ is at position 5 and $R^2$ is R as defined above;
n is 1;
$R^3$ is hydroxy, $C_{1-6}$alkoxy or lower(alkanoylaminoalkoxy);
Y is oxygen, sulfur, $CH_2$— or with the proviso that when Y is H, R is absent; and
Z is —S—, —$CH_2$— or halo with the proviso that when Z is halo, $R^2$ is absent
comprising:

(a) optionally hydrolyzing a compound of formula (I) under basic conditions to form the racemic mixture of the compound of formula (I) wherein $R^3$ is OH;
(b) treating the racemic mixture with an optically pure asymmetric alcohol of formula R°OH wherein R° is asymmetric loweralkyl or (R)-(+)-α-phenethyl to form diastereomeric esters of formula ($\pm$)-II:

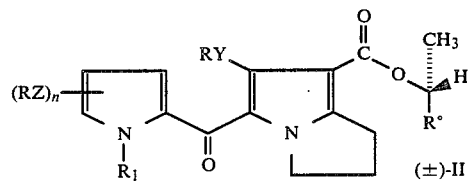

(c) resolving, by concomitant isomerization and fractional crystallization, ($\pm$)-II of step (b) to (−)-II isomer in the presence of a non-nucleophilic strong base, which is selected from a group consisting of tri-$C_{1-6}$alkylamine; pyridine; 2,4-dimethylpyridine; 1,5-diazabicyclonon-5-ene; and 1,8-diazebicycloundec-7-ene and which base is capable or rapidly isomerizing the diasteroemeric esters to a racemic mixture of 1:1 mixture of ($\pm$)-(II) but not capable of hydrolyzing the esters; and
(d) converting (−)-II to (−)-I via transesterification or hydrolysis without racemization under acidic and low temperature conditions.

2. The process of claim 1 wherein
R is $C_{1-3}$ alkyl or absent;
$R^1$ is hydrogen or methyl;
$R^2Z$ is at position 5 and $R^2$ is R as defined above;
n is 1;
$R^3$ is hydroxy, $C_{1-6}$ alkoxy or acetamidoethoxy;
Y is oxygen, $CH_2$— or H with the proviso that when Y is H, $R^2$ is absent; and
Z is —S—, —$CH_2$—, or halo with the proviso that when Y is halo, $R^2$ is absent.

3. The process of claim 1 wherein the optically pure asymmetric alcohol is (R)-(+)-α-phenethyl alcohol.

4. The process of claim 1 wherein the non-nucleophilic strong base is 1,5-diazabicyclonon-5-ene.

5. The process of claim 1 wherein the compound to be resolved is 5-(1-methyl-5-methylthiopyrrol-2-oyl)-1,2-dihydro-6-methyl-3H-pyrrolopyrrole-2-carboxylic acid or an ester thereof.

* * * * *

UNITED STATES PATENT AND TRADEMARK OFFICE
CERTIFICATE OF CORRECTION

PATENT NO. : 4,622,407
DATED : November 11, 1986
INVENTOR(S) : William K. Hagmann It is certified that error appears in the above—identified patent and that said Letters Patent is hereby corrected as shown below:

Title page, line 3 of the title itself, change "2-carboxylic acid" to --1-carboxylic acid--.

Under abstract, line 3, change "-2-carboxylic acid" to --1-carboxylic acid--.

Col. 1, line 4, change "PYRROLE-2" to --PYRROLE-1--.

Col. 4, line 37, change "lcar" to --1-car--.

Col. 6, line 43, change "2-carboxylate" to --1-carboxylate--.

Col. 8, line 47, change "2-carboxylic" to --1-carboxylic--.

Signed and Sealed this

Thirty-first Day of March, 1987

Attest:

DONALD J. QUIGG

Attesting Officer

Commissioner of Patents and Trademarks